United States Patent
McNair

(10) Patent No.: US 11,622,729 B1
(45) Date of Patent: *Apr. 11, 2023

(54) BIOMECHANICS ABNORMALITY IDENTIFICATION

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, KS (US)

( * ) Notice: Subject to any disclaimer, the term of this patent is extended or adjusted under 35 U.S.C. 154(b) by 429 days.

This patent is subject to a terminal disclaimer.

(21) Appl. No.: 16/898,709

(22) Filed: Jun. 11, 2020

Related U.S. Application Data

(62) Division of application No. 14/952,646, filed on Nov. 25, 2015, now Pat. No. 10,716,517.

(60) Provisional application No. 62/084,991, filed on Nov. 26, 2014.

(51) Int. Cl.
*A61B 5/00* (2006.01)
*A61B 5/0205* (2006.01)

(52) U.S. Cl.
CPC ........ *A61B 5/7267* (2013.01); *A61B 5/02055* (2013.01); *A61B 5/486* (2013.01); *A61B 5/7275* (2013.01); *A61B 5/742* (2013.01)

(58) Field of Classification Search
CPC ... A61B 5/7267; A61B 5/02055; A61B 5/486; A61B 5/7275; A61B 5/742; A61B 5/0205; A61B 5/1114; A61B 5/1121; A61B 5/1123; A61B 5/1128; A61B 5/4839

See application file for complete search history.

(56) References Cited

U.S. PATENT DOCUMENTS

| | | | |
|---|---|---|---|
| 6,561,992 B1 | 5/2003 | Eberhart et al. | |
| 6,832,251 B1 | 12/2004 | Gelvin et al. | |
| 7,496,561 B2 * | 2/2009 | Caudill | G06F 16/3347 |
| 8,126,736 B2 * | 2/2012 | Anderson | A61B 34/10 705/2 |
| 8,206,325 B1 | 6/2012 | Najafi et al. | |
| 8,273,036 B2 | 9/2012 | Fong | |
| 8,515,549 B2 | 8/2013 | Panken et al. | |
| 8,764,651 B2 | 7/2014 | Tran | |
| 8,821,416 B2 | 9/2014 | Johansson et al. | |
| 8,950,864 B1 * | 2/2015 | Massengill | A61B 5/4064 382/117 |

(Continued)

OTHER PUBLICATIONS

"The Comprehensive R Archive Network", R, Available online at: <http://cran.r-project.org>, Retrieved on Feb. 27, 2020, 1 page.

*Primary Examiner* — May A Abouelela
(74) *Attorney, Agent, or Firm* — Kilpatrick Townsend & Stockton LLP

(57) ABSTRACT

A system, method and article of manufacture are presented for assisting the fields of health care, kinesiology, and sports medicine. More specifically the method of the system measures the dynamics of the biomechanics of motion of a human patient or athlete and quantitatively determining the presence or absence of biomechanical abnormalities, classifying abnormalities that are present, developing or critiquing one or more diagnoses in terms of the biomechanics evidence supporting the classification, recommending an appropriate training or treatment regimen based on the diagnoses, and monitoring progress while the individual is under the training or treatment regimen.

20 Claims, 8 Drawing Sheets

(56) References Cited

U.S. PATENT DOCUMENTS

| | | | |
|---|---|---|---|
| 9,078,478 B2* | 7/2015 | Ross, Jr. | A61B 5/6804 |
| 9,412,161 B2* | 8/2016 | Varaklis | A61B 5/1128 |
| 9,414,776 B2* | 8/2016 | Sillay | A61B 5/14542 |
| 9,962,083 B2* | 5/2018 | Horseman | A61B 5/1113 |
| 10,198,499 B1 | 2/2019 | McNair et al. | |
| 10,431,336 B1 | 10/2019 | Murrish et al. | |
| 10,520,378 B1* | 12/2019 | Brown | A61B 5/7267 |
| 10,631,751 B2* | 4/2020 | Miyazaki | A61B 5/4528 |
| 10,716,517 B1 | 7/2020 | McNair | |
| 2004/0236604 A1 | 11/2004 | McNair | |
| 2005/0240086 A1 | 10/2005 | Akay | |
| 2006/0020177 A1 | 1/2006 | Seo et al. | |
| 2006/0252999 A1 | 11/2006 | Devaul et al. | |
| 2007/0021689 A1 | 1/2007 | Stergiou et al. | |
| 2007/0112287 A1 | 5/2007 | Fancourt et al. | |
| 2008/0275309 A1 | 11/2008 | Stivoric et al. | |
| 2009/0060287 A1 | 3/2009 | Hyde et al. | |
| 2009/0299232 A1 | 12/2009 | Lanfermann et al. | |
| 2009/0318779 A1 | 12/2009 | Tran | |
| 2011/0066010 A1 | 3/2011 | Moon et al. | |
| 2011/0111014 A1 | 5/2011 | Langston | |
| 2011/0137138 A1 | 6/2011 | Johansson et al. | |
| 2012/0083714 A1 | 4/2012 | Yuen et al. | |
| 2012/0095300 A1 | 4/2012 | McNair | |
| 2013/0012802 A1* | 1/2013 | Horseman | A61B 5/0022 600/545 |
| 2013/0079602 A1 | 3/2013 | Picard et al. | |
| 2013/0116514 A1* | 5/2013 | Kroner | A61B 5/316 600/509 |
| 2013/0158368 A1 | 6/2013 | Pacione et al. | |
| 2013/0181988 A1 | 7/2013 | Yoo et al. | |
| 2014/0039274 A1 | 2/2014 | Sarrafzadeh et al. | |
| 2014/0254883 A1 | 9/2014 | Kim et al. | |
| 2014/0316230 A1* | 10/2014 | Denison | A61B 5/168 600/545 |
| 2014/0336539 A1* | 11/2014 | Torres | A61B 5/162 600/595 |
| 2014/0343460 A1 | 11/2014 | Evans et al. | |
| 2014/0357968 A1* | 12/2014 | Chen | A61B 5/7278 600/309 |
| 2014/0371599 A1* | 12/2014 | Wu | A61B 5/0022 600/476 |
| 2015/0045699 A1* | 2/2015 | Mokaya | A61B 5/7257 600/595 |
| 2015/0072326 A1* | 3/2015 | Mauri | A63B 24/0006 434/247 |
| 2015/0080675 A1* | 3/2015 | Shin | A61B 5/721 600/301 |
| 2015/0272500 A1 | 10/2015 | Kan-tor et al. | |
| 2015/0351680 A1* | 12/2015 | Gordon | G16H 50/20 600/595 |
| 2016/0015312 A1* | 1/2016 | Yu | A61N 1/0492 600/595 |
| 2016/0143594 A1* | 5/2016 | Moorman | A61B 5/7246 705/2 |
| 2016/0198998 A1* | 7/2016 | Rahimi | A61B 5/4082 600/595 |
| 2016/0235323 A1* | 8/2016 | Tadi | A61B 5/1128 |
| 2016/0256082 A1* | 9/2016 | Ely | A61B 5/681 |
| 2016/0262687 A1 | 9/2016 | Vaidyanathan et al. | |

* cited by examiner

|     | V1 | V2 | V3 | ... | V135 | V136 | V137 | V138 | V139 | ... | V146 | V147 |
|-----|------|------|------|-----|--------|--------------------------|----------|-------------------|----------|-----|-------|-------------|
| SAMPLE | TEST1 | TEST2 | TEST3 | ... | TEST135 | DIAGNOSIS D1 | TIME D1 | DIAGNOSIS D2 | TIME D2 | ... | O2 | HEART RATE |
| SAMP1 | 32.93 | 23.95 | 77.08 | ... | 19.66 | | | | | ... | 98.57 | 57.82 |
| SAMP2 | 45.42 | 66.40 | 46.39 | ... | 42.13 | | | | | ... | 76.51 | 47.83 |
| SAMP3 | 39.16 | 59.53 | 42.49 | ... | 47.75 | RIGHT KNEE REPLACEMENT | 186 DAYS | FOREARM FRACTURE | 537 DAYS | ... | 47.99 | 33.56 |
| SAMP4 | 58.91 | 70.90 | 65.83 | ... | 50.56 | | | | | ... | 71.68 | 52.70 |
| SAMP5 | 59.43 | 31.21 | 59.56 | ... | 61.79 | ROTATOR CUFF TENDONITIS | 2 DAYS | | | ... | 41.33 | 67.58 |
| SAMP6 | 48.22 | 53.47 | 54.51 | ... | 35.11 | LOW BACK MUSCLE STRAIN | 1 DAY | | | ... | 33.82 | 54.75 |
| SAMP7 | 57.31 | 60.91 | 50.64 | ... | 77.24 | | | | | ... | 58.79 | 48.41 |
| ... | ... | ... | ... | ... | ... | | | | | ... | ... | ... |
| SAMP268 | 53.57 | 72.21 | 62.11 | ... | 35.11 | ROTATOR CUFF TEAR | 90 DAYS | | | ... | 81.66 | 68.40 |

| ITEM | VALUE |
|---|---|
| SENSITIVITY | 72% |
| SPECIFICITY | 79% |
| ABNORMALITY PREVALENCE | 62% |
| COHEN'S KAPPA | 0.82 |

*FIG. 4*

```

# CERDSM 14-MAY-2014 motion biclustering to detect and classify biomechanics
abnormalities library(biclust)
library(superbiclust)
# source("http://bioconductor.org/biocLite.R")
# biocLite("fabia")
library(fabia)

# superbiclust biclustering found by factor analysis where both the factors and the
loading matrix are sparse.
# FABIA is a multiplicative model that extracts linear dependencies between
samples and feature patterns.
# FABIA captures realistic non-Gaussian data distributions with heavy tails as
observed in gene expression measurements.
FABIA works less well with binomial data read table containing 268 cases with 135 biomechanics variables measured
res <- read.csv(file="c:/0_cerdsm/0__healthe_athlete/
dynamic_athletics_rebekah_mark/res3.csv")
res <- t(as.matrix(res))

# identify upper and lower outliers beyond 10th and 90th quantiles
ol <- matrix(rep(0, 270), nrow=2, ncol=135)
for (i in 1:135){
  ol[1,i] <- quantile(res[i,], 0.10)
  ol[2,i] <- quantile(res[i,], 0.90)
} transform raw values to ordinal values according to quantile membership
resq <- matrix(rep(0,36180), nrow=135, ncol=268)
for (i in 1:135){
  for (j in 1:268){
    if (res[i,j] < ol[1,i]) resq[i,j] <- -pi;
    if (res[i,j] > ol[2,i]) resq[i,j] <- pi;
  }
}
```

CONTINUES TO FIG. 5B

*FIG. 5A*

CONTINUED FROM FIG. 5A

.
.
.

```
# perform FABiA factor-analysis for bicluster acquisition
set.seed(1239)
fab <- fabia(resq, p=4, alpha=1e-03)

# transform FABiA output to construct bicluster set
outbcs <- BiclustSet(fab)
outbcs identify 135x4 markers assoc w/ clusters
outbcs@GenesMembership[,]
which(outbcs@GenesMembership[,1])
which(outbcs@GenesMembership[,2])
which(outbcs@GenesMembership[,3])
which(outbcs@GenesMembership[,4])

# identify 4x268 clusters assoc w/ cases
outbcs@ColumnMembership[,]
which(outbcs@ColumnMembership[1,])
which(outbcs@ColumnMembership[2,])
which(outbcs@ColumnMembership[3,])
which(outbcs@ColumnMembership[4,])

# generate plots of clusters and memberships of cases in clusters
extractPlot(fab)
```

*FIG. 5B*

BIOMECHANICS ABNORMALITY IDENTIFICATION

CROSS-REFERENCE TO RELATED APPLICATIONS

This application is a divisional application of U.S. application Ser. No. 14/952,646, filed on Nov. 25, 2015, and titled "Biomechanics Abnormality Identification," which claims the benefit of U.S. Provisional Application No. 62/084,991, filed on Nov. 26, 2014, and titled "Biomechanics Abnormality Identification," each of which is expressly incorporated by reference in its entirety.

BACKGROUND

Musculoskeletal diseases, which include back pain, arthritis, bodily injuries, and osteoporosis, are reported by persons in the United States more than any other health condition. In 2004, the estimated total cost of treatment and lost wages associated with musculoskeletal diseases was $850 billion, approximately 8% of the gross domestic product (GDP), and the estimated cost for treating patients with musculoskeletal conditions was $510 billion.

More than three of every five accidental injuries that occur annually in the United States are to the musculoskeletal system. In 2004, more than 57.2 million musculoskeletal injuries were treated in health care settings, accounting for 60% of injuries of all types treated that year. Musculoskeletal injuries include sprains and strains, usually incurred during sudden movement or over-use, (16.3 million injuries in 2004); fractures (15.3 million); open wounds and other open traumatic injuries (10.3 million); and contusions and bruises and other closed traumatic injuries (8.4 million). The estimated cost in 2004 of treating all musculoskeletal injuries was $127.4 billion. Since 1996, in 2004 dollars, the cost of treating musculoskeletal injuries has risen 37%. The share of cost attributed to prescription drugs rose from 11% in 1996 to 17% in 2004.

Thus, musculoskeletal conditions and their management are important epidemiologically and economically. Therefore, systematic and efficient diagnosis and management of these conditions have high clinical and financial value, not only in terms of direct expense, but also in terms of absenteeism among persons of employment age and lost productivity.

SUMMARY

Systems, methods, and computer-readable media are provided for the automatic identification of patients or athletes who have an existing disability or an acute or chronic injury, or who have an elevated near-term risk of musculoskeletal injury or disability, or healthy individuals whose musculoskeletal performance characteristics are the subject of optimization, training, or injury-prevention efforts. An embodiment is directed to classification and diagnosis, risk stratification, and optimization of assessment, communication, and decision-making to prevent or manage musculoskeletal injury in humans. An embodiment takes the form of a platform for analyzing 3-D motion data from high-speed multi-camera imaging devices with embedded decision support software for calculating biclusters. An embodiment takes the form of a 3-D digital motion-capture system that is connected via network to a decision support system that implements biclustering in a web-based cloud computing configuration. Thus, the aim of an embodiment relates to automatically identifying persons who potentially have a plurality of materialized abnormal musculoskeletal conditions or who have features that may dispose such persons toward such abnormal conditions by using signal-processing software and statistical predictive algorithms. This system calculates biclusters and bicluster membership properties of multi-variable static or dynamic biomechanics data acquired by the motion-capture system to enable detection and categorization of such abnormalities or predisposing features.

The measurements and predictive and classificatory algorithms enable use in sports medicine and rehabilitation and other ambulatory environments, as well as in general acute-care and chronic-care venues, and afford a degree of robustness against variations in individual anatomy and session-to-session variations in movements executed by an individual. An embodiment provides a leading indicator of likely near-term future abnormalities, proactively notifying clinicians responsible for the care of the individual and providing the care providers sufficient advance notice to enable effective preventive maneuvers to be undertaken. In an embodiment, involving serial testing of a given individual, a clinician is notified of actionable changes in classification and bicluster membership of an individual—either favorable or unfavorable—for the purposes of adjusting the regimen for managing the individual's condition(s). In an exemplary embodiment, a device is integrated with case-management software and electronic health record decision-support systems, including occupational health, health insurance, and disability assessment decision-support systems.

BRIEF DESCRIPTION OF THE DRAWINGS

The present invention is described in detail below with reference to the attached drawing figures, wherein:

FIG. 3 depicts a portion of an expert database in accordance with an embodiment of the invention;

FIG. 4 depicts a statistical display related to an exemplary embodiment of personal health evaluation; and FIGS. 5A and 5B illustratively provide an example embodiment of a computer program routine for evaluating risk of movement.

DETAILED DESCRIPTION

Figure 1A:
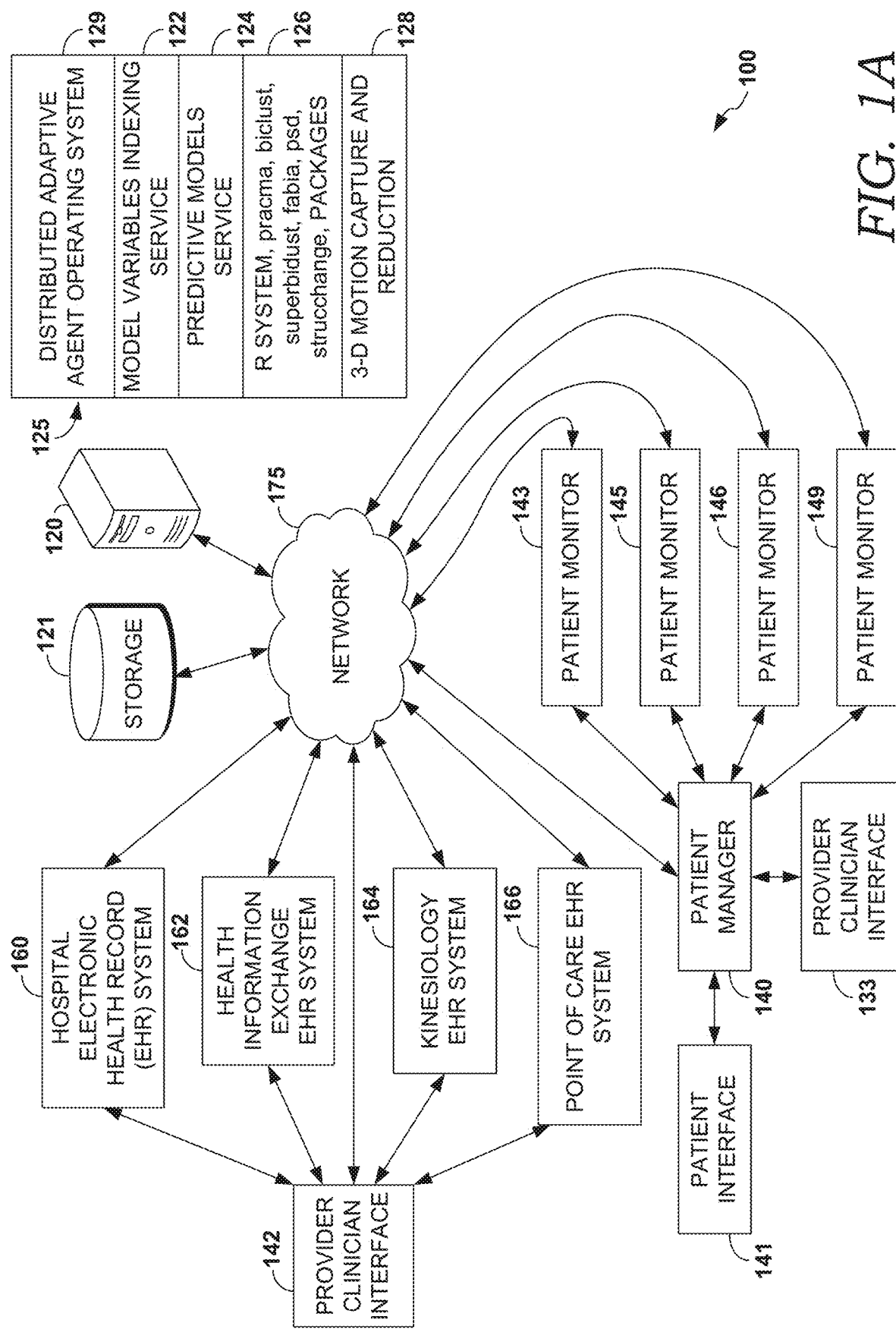
FIGS. 1A, 1B, and 1C depict aspects of an exemplary operating system environment suitable for practicing an embodiment of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things, a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer storage media and communications media. Examples of stored information include computer-useable instructions, data structures, program modules, and other data representations. Computer storage media examples include, but are not limited to, information-delivery media, RAM, ROM, EEPROM, flash memory or other memory technology, CD-ROM, digital versatile discs (DVDs), holographic media or other optical disc storage, magnetic cassettes, magnetic tape, magnetic disk storage, other magnetic storage devices, and other computer hardware or storage devices. These technologies can store data momentarily, temporarily, or permanently.

For most individuals for whom the musculoskeletal condition is unremitting or progressive, detailed physical medicine and biomechanics assessments are employed to establish the nature of the condition and the condition's prognosis, as well as to guide detailed prescription of treatment.

Some methods for kinesiologic and biomechanical testing and diagnosis of persons with musculoskeletal injuries or musculoskeletal diseases are sensitive to, and may be compromised or entirely confounded by, individual variations in patient anatomy and activities, including prosthetic devices and implantable medical devices, patient movement and positioning, diurnal and performance-to-performance variations when specific movements are measured repeatedly, etc. Moreover, other methods are sensitive to, and may be compromised or entirely confounded by, individual variations in operator positioning of the motion-capture equipment on or around the patient or variations in the timing and method of acquiring the data that will enter into the prediction and classification. Thus, one major deficiency of other methods is a high false-negative error rate and undue sensitivity to differences in execution of the measured movements.

A further deficiency of some methods is an untoward degree of activity-specificity—for example, a limited ability to detect compensatory changes in motion that occur subsequent to an injury or during recovery. Compensatory changes often arise when enablement of motion that ordinarily is enabled by the injured body part(s) is transferred to other body structures. Such compensatory changes may or may not be extinguished as the injured structure heals, strength is regained, and function is normalized.

Rather than taking only a few measurements of one or a few body parts' motion into account at a time, holistic assessment of biomechanical inter-relationships among anatomical structures preferably encompasses many dozens or even hundreds of simultaneous measurements of structures throughout the body as a whole, to properly account for the static and dynamic relationships among the many body parts.

An embodiment examines mathematical bicluster properties of the measured static and dynamic biomechanics data. In an embodiment, gait analysis and motion-capture equipment is used, followed by a detailed multi-variable analysis of long-time series 3-D digital biomechanics data. An embodiment uses analysis that goes beyond one or a few body structures at a time, such as the knee or hip. An embodiment performs detailed analysis over the recorded 3-D motion-capture data, even when only a small portion is typically thought to be relevant for analysis, and generally would have been discarded, unexamined or ignored by other approaches.

Thus, an apparatus that is non-invasive, accurate in its characterization of whole-body biomechanics based on time series acquired over several minutes, and that accommodates a wide range of body morphologies and variations in movement mechanics would be welcomed. Important adverse outcomes would be prevented, and care provider resources would be better conserved than typically would otherwise happen with qualitative and manual estimation by other methods.

Other attempts or efforts are deficient due to:

(1) Excessive false-negative diagnosis rate, especially for multiple concomitant conditions.

(2) Only emit, at most, one diagnostic when concomitant conditions are present.

(3) Confounding by individual variations in patient anatomy and activities, including prosthetic devices and implantable medical devices.

(4) Confounding by diurnal performance-to-performance variations when specific movements are measured repeatedly.

(5) Confounding by individual variations in operator positioning of the motion-capture equipment on or around the patient or variation in the timing and method of acquiring the data.

(6) Only a few measurements or a few isolated body parts' motion are taken into account at a time.

In light of the foregoing, an improved predictive-classificatory method and system is herein described. In an embodiment, prediction classification or decision-support alert signals emitted by the system are provided at logistically convenient times so as to enable effective preventive or therapeutic intervention in many of cases. Moreover, an embodiment is amenable to use by an outpatient athletic trainer, kinesiologist, or sports medicine office or clinic with limited space and staff resources, and is suitable for a much larger population who are at moderate risk of, or during recovery from, musculoskeletal injury. Such a system would find use as a tool, not only for surveillance and triaging the patients who present with movement-related complaints to hospitals and other acute-care venues, but also for ambulatory, free-living individuals who have one or more risk-factors for musculoskeletal injury or disability.

Effective preventive interventions vary, and optimal selection and personalized tailoring of them will depend upon the patient's context, gender, age, fitness, medications, comorbid diagnoses, history of previous injuries, and other factors. In the case of a moderately symptomatic ambulatory person, effective preventive interventions may include consultation with the personal trainer, kinesiologist, physical therapist, physician, or nurse for adjustment of regimen and activity recommendations. In the case of a person with existing, known orthopedic conditions, effective preventive interventions may include referral to a physician, a kinesiologist, or a physical therapist for adjustment of the training or rehabilitation regimen, or other alternatives.

The method of the subject system is useful in gate-keeping decisions regarding "step" therapy with agents such as platelet-rich plasma (PRP) injections, intra-articular ADAMTS-5 inhibitor or corticosteroid injections, or in implementing intensified monitoring with case-management services—interventions that are applied according to cost-effectiveness policies that select patients according to criteria that warrant the incremental expense. The method of the subject system may also be of use in disability ascertainment and detection of cases of malingering.

To classify biomechanics and identify pathological movement, static measures have long been the preferred method. Dynamic measures can be less burdensome to obtain, and can also be used. Accurately measuring and categorizing static and dynamic abnormalities in complex biomechanical structures remains a difficult, error-prone task. For example, the shoulder is complex and comprised of many moving parts. Motion abnormalities manifested in shoulder movements may cause secondary and compensatory changes in motions of the spine, torso, and trunk. However, in this example, the biomechanics measurements of the foot and lower extremity motion are unlikely to be affected by abnormalities in the shoulder.

High-dimensionality data pattern profiling is today readily accessible with the development of new technologies. Microarray plates and next-generation sequencing are exemplars of high-dimensionality data in the field of genomics. High-speed 3-D motion-capture systems generate high-dimensionality data and represent comparable advances in the fields of biomechanics and kinesiology. High-dimensionality technologies typically necessitate advanced analysis tools to deal with massive amounts of data that the measurements produce. Technical challenges include a huge number of variables (genes or biomechanics markers) as compared to the number of samples, high data noise levels, and difficulties with overlapping clusters and the instability of the resulting clusters as more cases accrue and as initialization parameters of the algorithm are adjusted slightly.

Clustering gene expression data has been an important problem in computational genomics. Clustering of biomechanics data is an important problem in computational kinesiology and sports medicine diagnostics. While some clustering methods, such as hierarchical and K-means clustering, have been shown useful in analyzing genomics microarray data, they have severe limitations. First, a biomarker or an experimental condition can be assigned to only one cluster. Second, all biomarkers and conditions may be assigned to clusters. However, biologically, a biomarker or a sample could simultaneously participate in multiple biological pathways. Conversely, a cellular process is generally active only under a subset of genes or experimental conditions, not all genes and all conditions. Correspondingly, a biomechanics biomarker could simultaneously participate in multiple mechanisms of injury, disability, or musculoskeletal performance, and, conversely, a particular biomechanical process is generally manifested only under a subset of biomechanics biomarkers or conditions, not all markers and conditions.

In an embodiment, clustering is an important type of unsupervised learning algorithm for data exploration and classification. Some clustering examples include K-means clustering and hierarchical clustering, both of which are widely used in biological research to find cancer subtypes and to stratify patients. These and other clustering algorithms depend on the quantitative similarity metrics (numerical distances) calculated using all of the markers or features. For example, individuals can be clustered into homogeneous groups by minimizing the summation of within-clusters sum of squares (summing the Euclidean distances) of their gene expression profiles. Unfortunately, this strategy fails when only a subset of features is informative (is active under a condition). This phenomenon can be demonstrated by K-means clustering results for an example using only the variables that determine the underlying true cluster compared with using all variables (which includes many uninformative variables). Clustering performance is sometimes poor when all variables are used in the clustering algorithm. Sparse clustering methods have been proposed to allow clustering decisions to depend on only a subset of feature variables (the property of sparsity). Prominent sparse clustering methods include sparse principal component analysis (PCA) and Sparse K-means, among others. However, sparse clustering still fails if the true sparsity is a local, rather than a global, phenomenon. More specifically, different subsets of features can be informative for some samples but not all samples, or, in other words, sparsity exists in both features and samples jointly.

A biclustering method produces marker and condition/sample clusters simultaneously. A biclustering method can model the situation where a marker or a condition is involved in several biological functions. Furthermore, a biclustering model can avoid those "noise" markers that are not active in any experimental condition. In analogous fashion, a biclustering method that analyzes biomarker and condition/subject clusters simultaneously can model the situation where a marker or condition is implicated in several musculoskeletal functions or compensatory changes to normal functions. Likewise, a biclustering model can avoid "noise" biomarkers that are not active in any health condition—either of injury or disability and recovery, or of elite training and athletic performance.

Biclustering algorithms mathematically produce clusters along two data dimensions (row and column) simultaneously. In an embodiment, a row represents an array of data drawn from a particular test subject, and a column represents a result for a single biological variable. Applying biclustering to high dimensionality data accommodates a particular process's effect on a subset of measures according to either causal or associative relationships, and a given measure can participate in several processes simultaneously, which may be concurrent/concomitant or otherwise temporally-related. To do this, markers-condition clusters should be defined with respect to sets of conditions-subjects clusters, respectively. The clusters so formed ought not to be exclusive of joint membership; each marker/condition should be able to belong to several clusters or no cluster, and each human subject should be able to belong to one or more clusters or no cluster.

There are several objectives when analyzing high-dimensionality data, such as grouping subsets of biomechanics metrics that are cross-correlated under subsets of concomitant conditions or classifying new biomarkers, given the distributional characteristics of other biomarkers with known classification and relationships. Discovering such cross-correlations can be useful to characterize biomechanics inter-relationships, such as compensatory changes following injury and propagation of abnormalities from one musculoskeletal structure to other structures. That is why it is important to make simultaneous clustering of columns (variables, metrics, biomarkers) and rows (samples/conditions) of the data matrices, to identify clusters of markers that are affected under clusters of conditions. This type of clustering is called 'biclustering,' and the resulting clusters are called 'biclusters.' A marker, or set of variables, can belong to more than one bicluster, and a condition can belong to more than one bicluster. Correspondingly, sampled subjects may have membership in more than one bicluster, as well. Furthermore, a biclustering model can avoid "noise" biomarkers that are not active in any clinical contingency or performance condition.

Biclustering algorithms can roughly be classified into three categories: combinatorial methods, e.g., Coupled Two-Way Clustering (CTWC), Order Preserving Submatrix (OPSM), Iterative Signature Algorithm (ISA), Binary Inclusion Maximal algorithm (BIMAX), association analysis based Range Support Patterns (RAP), Combinatorial Algorithm for Expression and Sequence-Based Cluster Extraction (COALESCE), nondeterministic greedy algorithms that seek biclusters, and Qualitative Biclustering (QUBIC); probabilistic and generative approaches such as Statistical-Algorithmic Method for Bicluster Analysis (SAMBA), Factor Analysis for Bicluster Acquisition (FABIA), particle swarm optimization and evolutionary algorithms; and matrix factorization methods like spectral clustering, Sparse Singular Value Decomposition (SSVD), and sparse singular value decomposition incorporating stability selection (S4VD). While biclustering performance has significantly improved in the past decade, data noise and bicluster overlaps make the problem still quite challenging. When data noise or bicluster overlap is high, most of the existing algorithms can only discover a small percentage of true biclusters that are latent in the data.

An embodiment provides a computerized system, method, and computer-readable media for automatically identifying persons who have or are at risk for musculoskeletal injury through the use of a computerized system. The measurements and predictive algorithms embedded within the system provide for unsupervised use in general acute-care and chronic-care venues and afford a degree of robustness against variations in individual anatomy and session-to-session movement execution. An embodiment provides a leading indicator of near-term future abnormalities, proactively alerting the clinicians caring for the person with sufficient advance notice to enable effective preventive maneuvers to be undertaken. In an exemplary embodiment, a device is integrated with case-management software and electronic health record decision-support system.

By way of example and not limitation, a user using an embodiment of the system may be able to perform designated movements to be measured in a 3-D motion-capture apparatus in an outpatient office or clinic for a short interval of time, such as ten minutes, for example, during which biomechanical kinetic, kinematic, and other measurements are acquired, and digitized at a sampling rate preferably not less than 10 Hz and not less than 12 bits precision. In an embodiment, a computer system processing the data acquired may include application software which, when executed, receives user data from the device, calculates a plurality of biomechanics measures, combines these in a mathematical bicluster model, identifies bicluster membership classification(s) for the individual, and communicates the classification results to a clinician, a user, case-management software, decision-support systems, or electronic health record systems. For example, the system may notify the user in advance via a notification message or electronic mail. In an embodiment, the system notifies a user's health plan, electronic-health record decision-support systems or personal health record systems via a call, HTTP, SMS text-message, or other form of electronic wireline or radiofrequency communication. In an embodiment, a notification includes a message indicating that the user has an increased likelihood of a near-term future abnormality or orthopedic abnormality occurrence. In an embodiment, a notification enables a care provider to take appropriate therapeutic or preventative measures.

As noted above, biclustering refers to a process of grouping markers and conditions simultaneously, producing a set of biclusters each including a marker set and a condition set. The marker values "1," "−1," and "0" indicate significant increase, decrease, and unchanged, respectively. Several important characteristics exist in bicluster recognition:

(1) There are various kinds of biclusters: markers and conditions can be positively and negatively correlated;

(2) Biclusters can overlap with each other in both marker dimension and condition dimension—since multiple pathways containing the same marker could be active under different conditions—multiple markers can influence each condition, and multiple conditions can be concomitant or comorbid;

(3) It is not necessary that each marker or condition has to participate in at least one bicluster (not necessarily full coverage)—some may be non-informative;

(4) Bicluster detection must be robust against heavy noise in the input data.

In an embodiment, non-overlap, full-coverage clustering methods are used to detect biclusters. In an embodiment, Factor Analysis for Bicluster Acquisition (FABIA) or other biclustering methods that are capable of supporting bicluster discovery in the context of substantial bicluster overlap and data noise are used. In an embodiment, biclustering methods that generalize the sparsity principle by considering samples and features as exchangeable concepts have been found to handle local sparsity, and so tend to perform well.

An exemplary operating environment as shown in FIGS. 1A, 1B, 1C, and 2 relates generally to the description of a system for biomechanics properties-based prediction and prevention of musculoskeletal abnormalities.

Turning now to FIG. 1A, there is presented an example operating environment 100 suitable for practicing an embodiment. Example operating environment 100 includes a computerized system for compiling and/or running an embodiment of an information architecture that performs a movement risk recommendation service. With reference to FIG. 1A, one or more electronic health record (EHR) systems, such as hospital EHR system 160, health information exchange EHR system 162, Kinesiology EHR system 164, point of care EHR system 166 are communicatively coupled to network 175, which is communicatively coupled to computer system 120. In an embodiment, components of operating environment 100 that are shown as distinct components may be embodied as part of or within other components of environment 100. For example, the one or more EHR systems 160-166 may be implemented in computer system 120. Similarly, a single EHR system may perform functions for two or more of the example EHR systems shown in FIG. 1A.

In an embodiment, network 175 includes the Internet, and/or one or more public networks, private networks, other communications networks such as a cellular network, or similar network(s) for facilitating communication among devices connected through the network. In an embodiment, network 175 is a local network or device interface such as a USB interface. Network 175 may be determined based on factors such as the source and destination of the information communicated over network 175, the path between the source and destination, or the nature of the information. For example, intra-organization or internal communication may use a private network or virtual private network (VPN).

Moreover, in some embodiments items shown communicatively coupled to network 175 may be directly communicatively coupled to other items shown communicatively coupled to network 175.

In an embodiment, operating environment 100 may include a firewall (not shown) between a first component and network 175. In such an embodiment, the firewall may reside on a second component located between the first component and network 175, such as on a server (not shown), or reside on another component within network 175, or may reside on or as part of the first component.

An embodiment of electronic health record (EHR) systems 160, 162, 164, and 166 includes one or more data stores of health records stored on storage 121. In an embodiment, a data store includes one or more computers or servers that facilitate the storing and retrieval of the health records. In an embodiment, one or more EHR systems 160, 162, 164, and 166 are implemented as a cloud-based platform or may be distributed across multiple physical locations. In an embodiment, EHR systems 160, 162, 164, and 166 further include record systems, which store real-time or near real-time patient (or user) information, such as information from wearable, bedside, or in-home patient monitors such as monitors 143, 145, 146, or 149, for example. Environment 100 includes input from a 3-D dynamic motion-capture system 143.

Although FIG. 1A depicts multiple example EHR systems, it is contemplated that an embodiment employs only one EHR system, or alternatively, relies on patient manager 140 and/or monitor 143 for storing and retrieving patient record information, such as information acquired from monitor 143.

Example operating environment 100 further includes provider clinician interface 142 communicatively coupled to the one or more EHRs 160, 162, 164, and 166. A clinician is broadly, a health professional, or a worker who serves a patient in a clinical setting, such as a doctor, kinesiologist, trainer, physical therapist, consultant, health aid, nurse aid, nurse, nurse practitioner, specialist, etc. In an embodiment, the clinician interface 133 is coupled to patient manager 140. Although environment 100 depicts a direct communicative coupling between interface 142 and the one or more EHRs 160, 162, 164, and 166, it is contemplated that some embodiments of interface 142 may be communicatively coupled to the EHRs through network 175. Embodiments of interface 142 may take the form of a user interface operated by a software application or set of applications on a client computing device, such as a personal computer, laptop, smartphone, or tablet computing device. In one embodiment, the application includes the PowerChart® software, manufactured by Cerner Corporation. In an embodiment, the application is a Web-based application or applet. Provider clinician application facilitates accessing and receiving information from a user or health care provider about a specific patient or set of patients for which movement analysis is to be performed and facilitates the display of results, recommendations or orders, for example. In some embodiments, interface 142 also facilitates receiving and displaying orders for the patient from the clinician/user, based on the results. In some embodiments, interface 142 may also be used to display patient information, such as orders, a set of variables, a set of patient records, a set of cluster characteristics, a set of samples, etc. Additionally, interface 142 is used to provide a report of individual performance, and to compare a first and second set of movement data, as discussed, for example, in connection to FIG. 2.

Example operating environment 100 further includes provider patient interface 141 communicatively coupled to storage 121, to computer 120, and to provider clinician interface 142. Although environment 100 depicts an indirect communicative coupling between interface 141 and the one or more patient monitors 143, 145, 146, and 149, it is contemplated that an embodiment of interface 141 resides on a patient monitor, such as 149. An embodiment of interface 141 takes the form of a user interface operated by a software application or set of applications on a client computing device, such as a personal computer, laptop, smartphone, or tablet computing device. In an embodiment, the application is a client/server application, a client application, a server application, a browser plugin, or a mobile phone application. In an embodiment, the application is a Web-based application or applet. A patient application facilitates receiving information and indications from a user or health care provider about a specific patient or set of patients for which analysis is to be performed and facilitates the display of reports, comparisons, results, recommendations, or orders, for example. In an embodiment, interface 141 also facilitates displaying a recommendation for a patient from a clinician based on results. In an embodiment, interface 141 is used to display patient regimen recommendations.

Example operating environment 100 further includes computer system 120, which may take the form of a server, which is communicatively coupled through network 175 to patient monitors 143, 145, 146, and 149; storage 121; and patient manager 140.

An embodiment of patient manager 140 takes the form of an application, which may be embodied as a software application operating on one or more mobile computing devices, tablets, smart-phones, front-end terminals in communication with back-end computing systems, laptops, or other computing devices. In an embodiment, manager 140 includes a Web-based application or set of applications that is usable to manage user services provided by embodiments of the invention. For example, in an embodiment, manager 140 facilitates processing, logging, evaluating, interpreting, comparing, reporting, accessing, storing, retrieving, and communicating information acquired from monitor 143. In some embodiments, manager 140 is used to produce and/or report and/or compare and/or display user (or patient) movement information, such as that illustratively provided in FIG. 3. Similarly, a user (who may be a patient) may access and view results of movement analyses of previously compiled data using manager 140. Moreover, in an embodiment of manager 140, an interface component is used to facilitate access or input by a user of information or functions related to monitor 143, such as operational settings or parameters.

As shown in example environment 100, manager 140, in an embodiment, is communicatively coupled to monitor 143 and to network 175. In an embodiment, monitor 143 communicates via network 175 to computer 120 and/or storage 121 and/or clinician interface 142. An embodiment of monitor 149 comprises one or more sensor components, e.g. sensor 181 or 189 (as shown in FIG. 1C) operable to acquire biometric or biological information about a user, such as information associated with a particular physical or mental state or the user, and which may be acquired periodically or as one or more time-series. In an embodiment, monitor 149 is a web form that receives information from a user indicating data related to one or more physiological variables. In an embodiment, monitor 145 comprises a sensor or probe component operable for sensing a user's temporal activity, such as sensing EEG signals derived from the user. In an embodiment, patient data is collected before the user performs a physical movement regimen. In an embodiment, patient data is collected after the user performs a physical movement regimen. In an embodiment, patient data is collected while a user performs a physical movement regimen. In an embodiment, data collected during a physical movement regimen is synchronized with one or more variables associated with a physical movement.

Turning briefly to FIG. 1C, patient physiological variables context diagram 700 illustrates a number of patient monitors (143, 145, 146, and 149) for sensing various types of physiological measurements of variables in a motion capture room context. A test area 101 uses a 3-D imaging device 143 capable of capturing 3-D data, as also shown in expanded view 102, which shows additional detail for some aspects. In an embodiment, imaging device 143 collects a set of 3-D motion data as a subject performs a regimen of physical movement. The test area includes a space to perform bodily physical movements in a regimen of movement, and a system to collect signals before, during, or after the movement comprising patient monitors 143, 145, 146, 149, patient manager 140, and exercise equipment 191. In an embodiment, exercise equipment 191 is absent from the test area and not used during physical motion. In an embodiment, the physical motion of the test subject is monitored while using exercise equipment 191. In an embodiment, exercise equipment 191 comprises a treadmill, an exercise ball, a stool, an elliptical trainer, one or more free-weights, an incline bench, a flat bench, one or more exercise stations of a universal gym, a skiing simulator, a skating simulator, a golfing simulator, a bat, a body blade, an exercise bike, an exercise wheel, a pressure sensitive mat, etc. In an embodiment, exercise equipment 191 has embedded patient monitor that couples to patient manager 140 through wireless interface 199. A monitor, such as patient monitor 145, may monitor muscle activity, which might be sensed from electromyogram signals, eye movement, which might be sensed from electrooculogram signals, or other biometric information. In an embodiment, a monitor, such as patient monitor 145, simply consists of a sensor probe, such as an EEG probe, and a communication link that periodically transmits identification information and probe data to interface 199, which in an embodiment, is a network interface on a computer that performs the operations of patient manager 140, so that the time series of monitored values is stored on patient manager 140, enabling an associated computer to perform patient manager functions, such as evaluating a data array for membership in a cluster, determining a condition associated with a cluster, and reporting individual performance, orders, and predicted risks. In an embodiment, patient monitor 143 collects raw sensor information, such as optical sensor, and performs signal processing, such as movement detection, kinematic modeling, distance and shape processing, velocity measurement, providing physiological-variable related data, trending, wavelet processing, thresholding, computational processing of time series, logical processing of data collected, etc. In an embodiment, the sensor 143 comprises an infrared projector. In an embodiment, the sensor 143 comprises an audio detector and/or an audio array detector. In an embodiment, sensor 143 includes an audio transmitter. In an embodiment, the sensor 143 is an array of optical sensors using passive light detection to form a 3-D image of a subject. In an embodiment, sensor 143 comprises a multi-camera, high speed digital video 3-D motion capture system, e.g. the Dynamic Athletics, Inc. system that captures and measures 135 biomechanics variables.

In an embodiment, a monitor, such as patient monitor 149, communicates through interface 141 with a patient manager 140 through wired or wireless network interface 198, thus allowing patient manager 140 to perform multi-sensor or single sensor processing. In an embodiment, interface 141 is one of an audio/microphone jack, a USB connector, a mini-USB connector, or a micro-USB connector. In an embodiment, a monitor, such as monitor 149, makes use of a fingertip oximetry probe, to collect data. In an embodiment, monitor 149 makes use of a first physiological-variable probe, such as non-invasive blood pressure monitor (NIBP) 181 and a second physiological-variable probe, such as cardiac probe cluster 189. Probe 181 is useful for irregularities in blood pressure, such as unusually high or low mean arterial pressure, diastolic pressure, or systolic pressure. Though monitor 149 is shown with two probe types, an embodiment of monitor 149 has an arbitrarily large number of probes for the same physiological variable or for many variables. In an embodiment, monitor 149 makes use of multi-sensor electrocardiogram probe 189. Probe 189 is useful for simultaneously measuring electrical activity of the heart and respiration rate for detection of heart rate, tachycardia, heart rate synchronized with movement exertion, etc. In an embodiment, probe 189 is used to detect respiration rate redundantly over three pairs of electrodes, allowing monitor 149 to collect data for breathing rate synchronized with movement exertion, etc. An embodiment of a probe, such as probe 189, monitors one or more of Pulmonary Capillary Web Pressure (PCWP), Left Atrium Pressure (LAP), Central Venous Pressure (CVP), Intra Cranial Pressure (ICP), Central Venous Oxygen Saturation (SCVO2), Hemoglobin Oxygen Saturation (SO2), Arterial Oxygen Saturation (SpO2), temperature, blood pressure, rate, temperature, or other physiological variable. An embodiment of monitor 146 tracks respiration directly through respiration probe 186. An embodiment of monitor 145 tracks temperature with a surface temperature probe. An embodiment of monitor 149 accumulates data over an observation period, and buffered data is transferred to patient manager 140 for non-real-time evaluation. An embodiment of monitor 145 includes a motion sensor, with accelerometer for sensing seizure, coughing, or motion.

In an embodiment, one or more sensor components of monitor 149 may comprise a user-wearable sensor component or sensor component integrated into a living environment, such as a hallway, or an exercise room. Examples of sensor components of monitor 149 include wherein the sensor is positioned on or near the user's head, attached to the user's clothing, worn around the user's head, neck, leg, arm, wrist, ankle, etc., skin-patch sensor, ingestible or subdermal sensor, or wherein sensor component(s) are integrated into the user's living environment, sensors operable with or through a smart phone carried by the user, for example.

An embodiment of monitor 149 stores user-derived data locally, and/or communicates data over network 175 to be stored remotely. In an embodiment, manager 140 is wirelessly communicatively coupled to monitor 145. Manager 140 may also be embodied as a software application or app operating on a user's mobile device. In some embodiments, manager 140 and monitor 143 are functional components of the same device, such as a device comprising a sensor and a user interface. In some embodiments, manager 140 is embodied as a base station.

The example embodiment of monitor 145 shown in FIG. 1C includes some functionality of manager 140. For example, this embodiment of monitor 145 includes a user interface with functionality for configuring operational settings, such as on and off or settings for storing and/or communicating test-related information acquired from the user information, such as uploading the information to manager 140 or to storage 121, and display functionality for viewing or reviewing test-related information acquired from a user.

Additionally, an example embodiment of monitor 149 is shown in FIG. 1C. In this embodiment, monitor 149 is worn on the user's hand and wrist while the user is performing physical movements. Further, in an exemplary embodiment, monitor 149 includes a probe 189 for sensing a cardiac signal. Additionally, the example embodiment of monitor 149 shown in FIG. 1C includes some functionality of manager 140. For example, this embodiment of monitor 149 includes a user interface with functionality for configuring operational settings, such as on and off or settings for storing and/or communicating biological information acquired from a user, and uploading the information to manager 140 or to storage 121, and display functionality for viewing or reviewing biological information acquired from the user. In an embodiment, monitor 149 is embodied as a Sotera™ sensor, such as that manufactured by Sotera Wireless, Inc. of San Diego, Calif.

With reference to FIG. 1A, an embodiment of monitor 145 includes analog-to-digital (A/D) converters for converting analog acquired information into digital information. For example, in one embodiment, user information is acquired at 512 samples per second.

In an embodiment, monitor 149 includes functionality for processing user-derived information locally or for communicating the information to computer system 120 or manager 140, where it may be processed. In an embodiment, the processing may be carried out or facilitated by one or more software agents, as described below. In an embodiment, the processing functionality, which may occur on monitor 149, manager 140, and/or computer system 120, includes signal conditioning, such as removing noise or erroneous information. In an embodiment, processing functionality is operable to process user-derived information, such as NIBP data, as it is acquired, continuously or periodically, such as every 10, 15, 30, or 60 seconds, every few minutes, or at the beginning or end of a regimen. In an embodiment, the data is reduced into a time series with resolution of 5, 10, 15, 30, 60 seconds, or every few minutes.

Computer system 120 comprises one or more processors operable to receive instructions and process them accordingly, and may be embodied as a single computing device or multiple computing devices communicatively coupled to each other. In an embodiment, processing actions performed by system 120 are distributed among multiple locations such as one or more local clients and one or more remote servers. In an embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

An embodiment of computer system 120 includes computer software stack 125, which in some embodiments operates in the cloud, as a distributed system on a virtualization layer within computer system 120. An embodiment of software stack 125 includes a distributed adaptive agent operating system 129, which may be implemented as a platform in the cloud, and which is capable of hosting a number of services such as 122, 124, 126, and 128. An embodiment of services 122, 124, 126, and 128 run as a local or distributed stack in the cloud, on one or more personal computers or servers such as system 120, and/or a computing device running manager 140. In an embodiment, manager 140 operates in conjunction with software stack 125.

In an embodiment, Model Variables indexing service 122 and predictive models service 124 provide services that facilitate retrieving frequent item sets, extracting database records, and cleaning the values of variables in records. For example, variables indexing service 122 may perform functions for associating a cluster model with a set of representative samples and/or a set of associated conditions. In an embodiment, predictive models service 124 determines a suggested order set from an associated condition. In an embodiment, predictive models service 124 predicts that a second condition is at risk given the cluster that a test sample belongs to. In an embodiment, predictive models service 124 associates an order set with a cluster and/or condition. In an embodiment, these services may invoke software services 126. Software services 126 perform statistical software operations, and include statistical calculation packages such as, in one embodiment, the R system (the R-project for Statistical Computing, which supports R-packages or modules tailored for specific statistical operations, is accessible through the Comprehensive R Archive Network (CRAN) at http://cran.r-project.org); R-system modules or packages including biclust, superbiclust and FABIA or similar services for computing a set of bicluster statistics for a data set, tsDyn or similar services for facilitating implementation of nonlinear autoregressive time series models, tuneR for performing statistical operations, pracma for performing practical numerical mathematical functions, tseriesChaos for nonlinear time series operations, strucchange for testing, monitoring and dating structural change, psd for estimating the power spectral density, wavelets for computing wavelet transforms, seewave for estimating entropy, and arulesSequences or similar services for facilitating operations such as K-nearest neighbor distance calculations. Software packages 126 are associated with 3-D motion capture and reduction services 128, which are operable to capture user physical movement and to produce an array of variables describing user movements during performance of a movement regimen.

Example operating environment 100 also includes storage 121 or data store 121, which in some embodiments includes patient data for a candidate patient and information for multiple patients; variables associated with patient recommendations; recommendation knowledge base; recommendation rules; recommendations; recommendation update statistics; an operational data store, which stores events, frequent item sets (such as "X often happens with Y," for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data stores associated with the one or more EHR systems, such as 160, 162, 164, and 166 and patient manager 140. Further, although depicted as a single storage data store, data store 121 may comprise one or more data stores, or may be in the cloud.

Figure 1B:
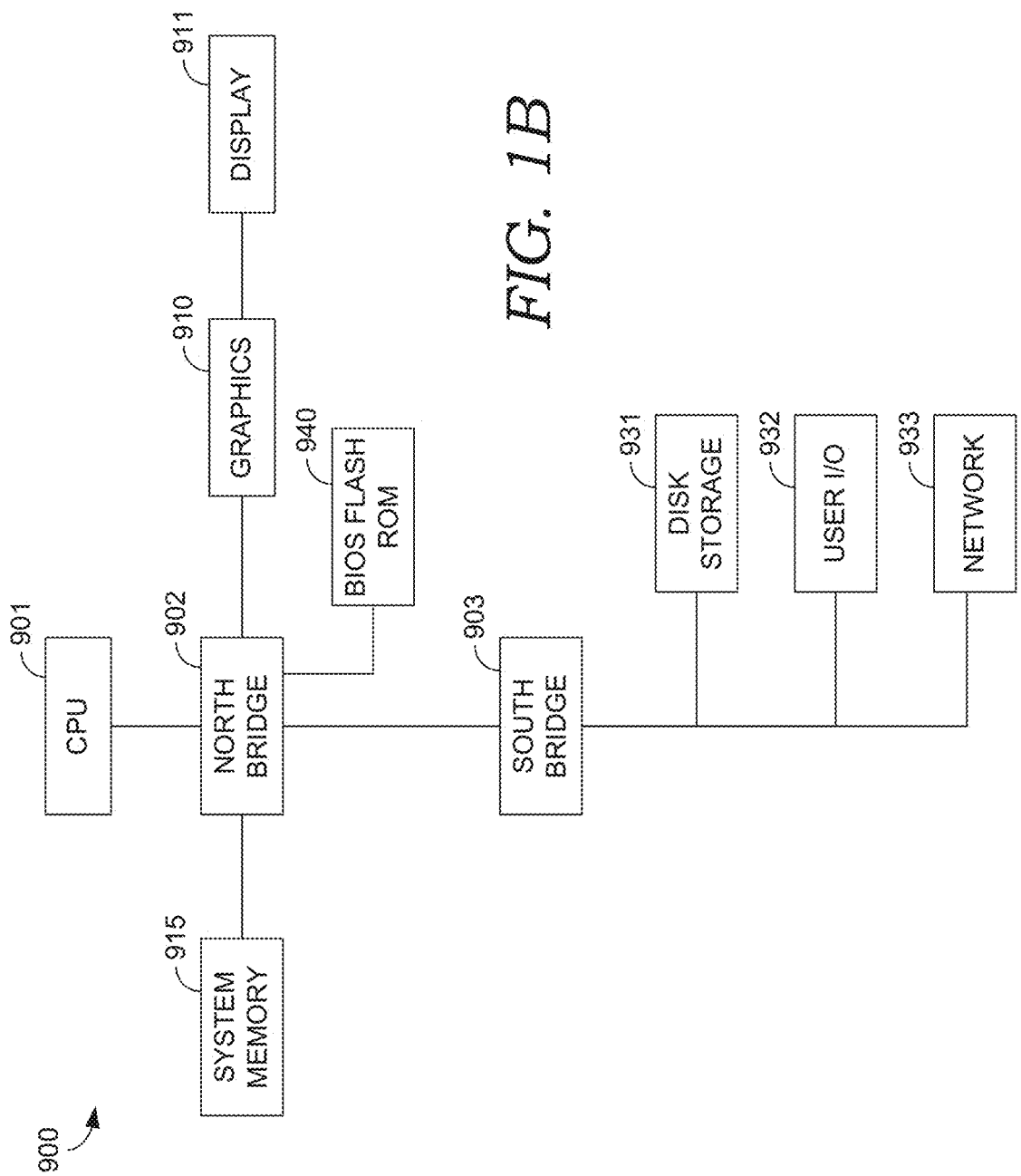
Figure 1C:
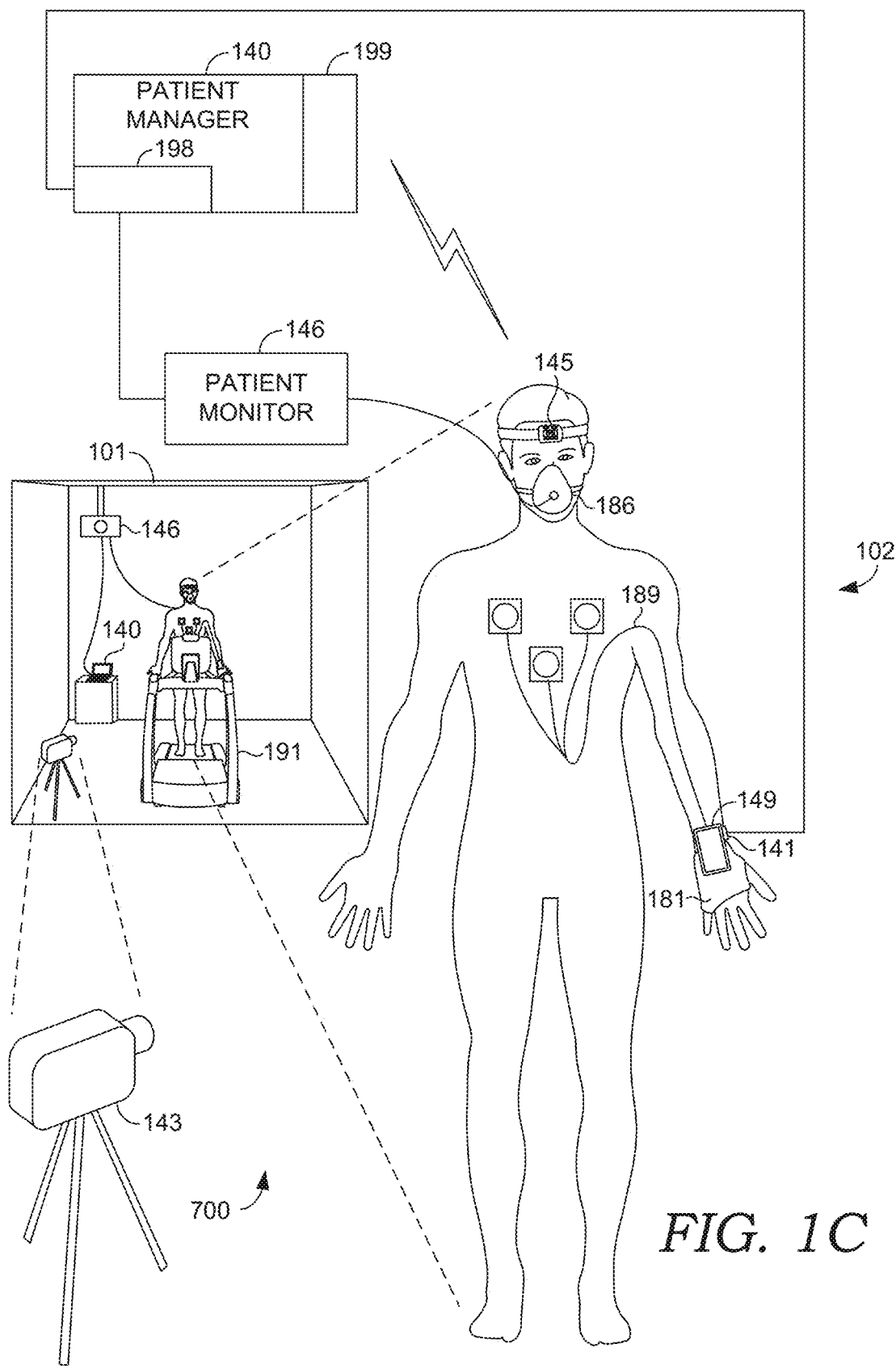

Turning briefly to FIG. 1B, there is shown one example embodiment of computing system 900 that has software instructions for storage of data and programs in computer-readable media. Computing system 900 is representative of a system architecture that is suitable for computer systems such as computing system 120, patient manager 140, patient monitor 149, and Kinesiology EHR system 164. One or more CPUs, such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931, such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in an embodiment, computer system 120 is a computing system made up of one or more computing devices. In an embodiment, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In an embodiment, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities, and choices that communicate via declarative messaging and use abstractions to allow for future adaptations and flexibility. An agent has its own thread of control, which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2:
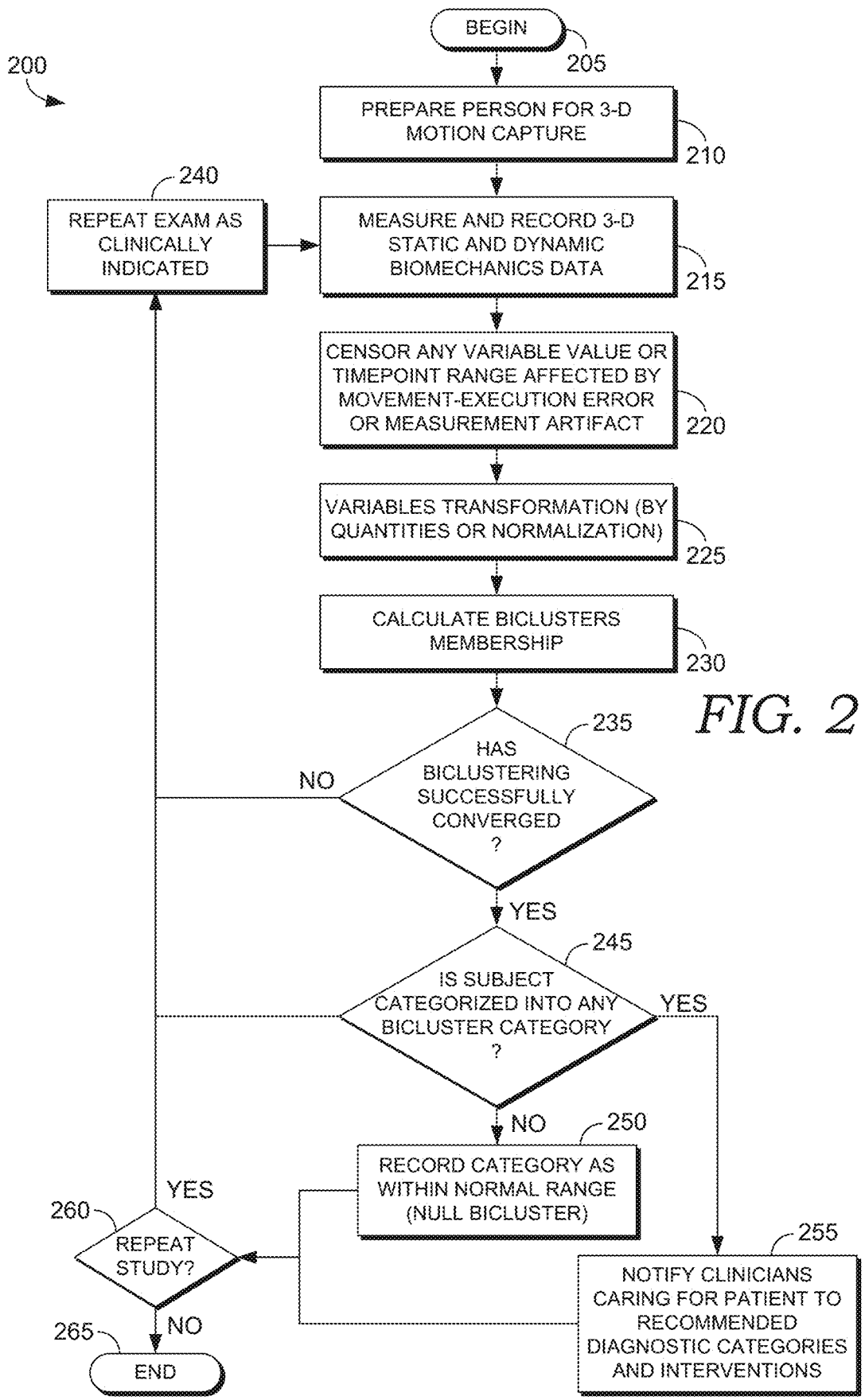
FIG. 2 depicts a flow diagram of a method of personal health evaluation in accordance with an embodiment of the invention.

Turning now to FIG. 2, there is depicted a representative flow diagram 200 of a method of movement evaluation. An embodiment relates generally to a system for biomechanics properties-based prediction and prevention of musculoskeletal abnormalities. In an embodiment, a clinician working with an application, such as a healthy subject application, assigns a regimen physical activity to a test subject and collects a set of 3-D motion data from a test subject who performs the assigned regimen. A parent database is formed having a variable array from each subject for a large number of subjects who have performed a variety of physical regimens. In an embodiment, the parent database consists of all the arrays formed from data from those test subjects who have performed a selected regimen. In an embodiment, a clinician selects a subset of the parent database to form an expert subset database that is relevant to a certain test subject. In an embodiment, the expert database is selected from a parent database by eliminating one or more reference arrays corresponding to test subjects because they are not similar to the present subject in attributes such as identity, origin, gender, age, level of fitness, body size, flexibility, athletic ability, injury status, time since injury, therapeutic regimen prescribed, regimen purpose, regimen class, regimen type, time since therapeutic regimen has been practiced, and diagnostic category. In an embodiment, the expert database is formed from the parent database by selecting one or more reference arrays based on a similarity to the test subject in one or more subject attributes. In an embodiment, a parent database is formed from a working age population to predict risks from the way that people move when they perform a regimen of physical motion. In an embodiment, risks of treatment are identified to a clinician from the clusters to which a test subject belongs. A body tends to compensate for injury, and risks from these altered movements may be detected and highlighted to a clinician based on subtle similarities between a test subject and others who have performed a similar regimen of physical motion in the expert database.

At 205, a process of physical motion evaluation begins. At 210, a subject is prepared for 3-D motion capture. In an embodiment, a subject dons tight fitting, uniformly colored apparel that provides a good contrast with the background of a test area 101. At 215, with collection sensor 143 focused on a test subject, the subject performs a regimen of physical activity. In an embodiment, the regimen is designed to collect a very broad range of physical motion including measurements for a number of body members (e.g., head, neck, trunk, upper arm, lower arm, foot, hand, lower leg, upper leg, etc.), for a number of measurements for each body member, such as body member angle, 3-D position, linear velocity, linear acceleration, jerk, impulse, work, force, power, momentum, angular velocity, angular jerk, angular impulse, angular acceleration, torque, etc.

In an embodiment, a video feed of 60 frames per second is collected and a wire frame is constructed for the test subject determining estimated location of each of the joints, and an estimated dimension for each body part. In an embodiment, an array is formed from the measurements drawn from the test subject while performing a regimen. The samples and variables are illustrated for example in FIG. 3. Each row 301-307, 368 holds a reference sample array associated with a test subject. Each column 310-313, 335-339, 346, and 347 holds a variable content associated with a variable name and variable type listed in the first and second topmost rows respectively in table 300. In an embodiment, motion variables denoted $V1, V2, \ldots V135$ are measured from sensor 143. In an embodiment, such motion variables alone number in the hundreds or thousands. In an embodiment, a diagnosis or condition variable $V136$ is recorded for a test subject along with a time of contraction for the condition $V137$. In an embodiment, a second diagnosis or condition variable $V138$ is recorded for a test subject along with a time of contraction for a second condition $V139$. In an embodiment, test subject personal variables such as height $V140$, weight $V141$, body mass index $V142$, gender $V143$, age $V144$, level of fitness $V145$ are recorded for the test subject at or near the time of testing. In an embodiment, test subject biological variables, such as oxygen saturation $V146$, heart rate $V147$, etc. are also collected and stored in an array representing the test subject during or near the performance of one or more components of a regimen of movement. In an embodiment, measured biological health variables comprise one or more of blood pressure, blood oxygen, heart rate, respiration rate, audio, temperature, gender, age, ability, weight, body mass index, flexibility, size, and athletic level. In an embodiment, the total number of variables monitored is M, so that the vector of available variables spans from V1 to VM. In an embodiment, the accuracy of cluster representation increases as M increases.

In an embodiment, at 220 raw variables describing the test subject for the regimen are cleaned to provide a representative array. In an embodiment, the test subject performs two or more repetitions of the regimen and the arrays collected are jointly processed to produce one representative array, e.g., by using a mean, median, trial count, rank order, or by composing variables from two or more trials into one representative array. For example, the regimen may be repeated three times, and the third repetition taken as representative, because it is likely to represent a fatigued state. In another example, the elements of each variable are rank ordered, and the median value is selected to represent each variable. In another example, the average of the valid data for each variable is formed to represent the variable.

In an embodiment, at 220 missing data is imputed in one or more values by statistical means. In an embodiment, data is imputed by one or more of a last observation carry forward method, a data simulation method, bootstrap method, generalized estimating equation method.

In an embodiment, at 225, the variables in an array are transformed into a standard scale. In an embodiment, a z-score is computed for a given variable across a distribution of a database population. In an embodiment, a normalization occurs, putting the variable into a standard scale, such as zero mean and unit standard deviation. In an embodiment, a variable transformation is performed to scale the data toward a normal distribution. In an embodiment, a quantile (an approximate percentage of deflection of the variable across a range) represents the value of a transformed variable.

At 230, bicluster membership for a data set is determined. In an embodiment, biclusters are computed for N reference arrays. In an embodiment, biclusters are computed for N reference arrays plus the subject array. In an embodiment, biclusters are computed using the R-System routines, such as biclust, superbiclust, and FABIA. In an embodiment, at 235 it is determined whether or not the biclustering has successfully converged. In an embodiment, an alpha parameter is used that tests whether or not an iterative bicluster computation technique has converged. In an embodiment, alpha is chosen to be 0.001. At 235, if biclustering has not successfully converged, then in an embodiment, additional exams are repeated as clinically indicated at 240, and the method proceeds to 215. In an embodiment, at least a dozen samples from at least a dozen individuals for a particular injury are accumulated to represent motion for that injury to be represented in a particular cluster. At 235, if the biclustering has successfully converged, the method proceeds to 245.

At 245, the biclusters determined by the technique are available to be processed. In an embodiment, N+1 samples are processed and ranked according to a similarity measure for each of K biclusters. In an embodiment, each bicluster Cn, for $1 \leq n \leq K$ has a set of samples Sn that exceed a first similarity threshold, and so are grouped as a set of samples that are representative of the bicluster. In an embodiment, each bicluster Cn, for $1 \leq n \leq K$ has a set of $j_n$ variables Vn1, Vn2, ... Vnj$_n$ identified by the biclustering technique that are determined to be variables that represent the similarity of the bicluster (a cluster marker). In an embodiment, each of the variables Vn1, Vn2, ... Vnj$_n$ exceed a second similarity threshold, and so are grouped together as the set of representative variables for cluster Cn. In an embodiment, a common threshold is used for all clusters. In an embodiment, a separate threshold is used for each cluster. In an embodiment, a cluster Cn is identified by a proper subset of the available variables so that $j_n$<M. In an embodiment, the number of variables representative of a cluster is much smaller than the total number of available variables, so that for example, $j_n$<M/4. In an embodiment, a set of variables is chosen as a marker that have the largest similarity within the cluster based on the number of variables that can be easily viewed by a clinician, such as the largest 12 variables.

At 245, it is determined whether or not a subject array is categorized into any bicluster category. In an embodiment, the subject array was included in the cluster membership calculation at 230, and so the category is simply determined by examining the characteristic sets of samples Sn. In an embodiment, the subject array was not included in the cluster membership calculation at 230, and the cluster membership is determined by computing a distance of the subject sample from each cluster mean for each cluster Cn using the cluster mean and the subject variables that are grouped as the set of representative variables for cluster Cn, namely Vn1, Vn2, ... Vnj$_n$. If the subject array is not categorized into any bicluster category, the method proceeds to 250, where the category is determined to be within the normal range (the null cluster). If on the other hand, one or more cluster categories of interest are identified, the method proceeds to 255.

In an embodiment, at 255, a cluster C1 is identified as associated with the subject array. In an embodiment, cluster C1 is characterized by evaluating conditions or diagnoses that appear in the set S1. In an embodiment, the diagnoses in the set S1 are classified according to similar group or bodily area (e.g., C1 is related to clavicular/glenohumeral abnormalities; C2 comprises uni/squat variables and measures deficits in lower-extremity force-development; C3 reveals interactions among trunk-thorax-lumbar spine; and C4 comprises uni/lunge/squat variables). In an embodiment, the frequent diagnoses or conditions or bodily areas are used to characterize cluster C1. For example, by counting the frequency of the bodily area within C1, the method determines that C1 is associated with shoulder injuries and lumbar injuries. At 255, a report is presented on a display to a user by way of a user interface message: "motion risks may include shoulder and lumbar for this subject." In an embodiment, the report is printed on paper. In an embodiment, a listing of conditions to be concerned about is presented. In an embodiment, the descriptions of conditions of concern are presented. In an embodiment, the frequently occurring or highly similar descriptions from one or more diagnosis fields within C1 are presented as part of a display.

In an embodiment, the display includes a view into sample arrays that are representative of cluster C1, such as a subset with shoulder injuries, a subset with lumbar injuries, or a subset with both shoulder and lumbar injuries. In an embodiment, the display includes the variables V11, V12, ... V1j$_1$. In an embodiment, a spectrum of injury area variables are presented to the user. For example, a spectrum of shoulder variables or lumbar variables are presented to the user. In an embodiment, a cluster mean of a set of variables is presented to the user. In an embodiment, the subject variables are presented. In an embodiment, a subset of cluster samples are at least partially presented and/or their averages, or other associated data. In an embodiment, an average time since injury is presented for a number of cluster samples nearest to the subject sample, having the same condition as the subject sample. In an embodiment, quantile data is displayed. In an embodiment, raw measurement data is presented.

In an embodiment, at 255, a predictive application is invoked to assemble an order set that is suggested based on a characterization of the cluster C1. An order set comprises a set of pain medications, a time period, a time duration, an amount of hydrotherapy, a set of therapeutic exercises, or a varied sequence of two or more of these items. For example, an order set for rotator cuff strengthening exercises is presented to a clinician for cosignature, together with a suggestion to the clinician to "consider modifying these exercises to avoid compensatory lumbar injury," and a dynamic link offering to add to the orders for the clinician a set of low-back safe stretching exercises. In an embodiment, an order set comprises characteristics derived from the chosen cluster. In an embodiment, an order set comprises information linked to the samples of a cluster through the condition, diagnosis, or injury area found to be frequent within the cluster. In an embodiment, an identified condition and a progress level is displayed. In an embodiment, an estimated recovery progress is estimated. For example, a statement is presented, "Normally healing anterior cruciate ligament tear," at 3 weeks of recovery.

At 260, a decision is made whether or not to repeat a study. If the decision is no, the method terminates at 265, otherwise the method returns to 240, where an exam is repeated as clinically indicated. In an embodiment, a study is repeated periodically by a subject as part of a recovery therapeutic regimen. At first, several examples are taken to get a baseline of behavior for this test subject. In an embodiment, data is collected from a large population of volunteers, and as the number of available samples in a parent database grows, the number of clusters that might be well-represented grows proportionately. In an embodiment, about a dozen samples of similar conditions is enough to get a set of variables somewhat representative of that condition.

In an embodiment, the method is used as a wide-scope screening exercise to identify initial areas of potential concern after an injury. For example, an exercise room at a ski resort offers concerned skiers the ability to run through a wide range of physical motions before being cleared to return to the slopes. In an embodiment, subjects could be evaluated before skiing to determine which difficulty level is appropriate for the movement characteristics of a subject. A subject comes to the exercise room complaining of wrist pain, and the injury is evaluated and determined to be a mild sprain, but as a precaution, the subject elects to undergo motion evaluation. The subject is evaluated and determined by the method of the system to belong to a cluster including Samp6, Samp7, and Samp68, which are presented to the clinician who sees rows 406, 407, and 468 of FIG. 3 together with descriptions of the variables in a header row, thus having the identified variables V1, V2, V3, and V135 as potentially relevant to the cluster. The clinician sees also the data from the current subject array Samp1, and recognizes that the subject is at the 19.66 percentile of variable V135, which is rotation movement around the right shoulder. Noticing that the nearest samples, Samp6 and Samp268, had mild rotator cuff injuries, the clinician elects to evaluate the right rotator cuff, and also to be careful in doing so, because the system has clustered a low back muscle strain as being in the same cluster. Therefore, this patient is deemed likely to have a rotator cuff injury with compensatory movement of the torso, perhaps leading to a low-back injury. Further tests are performed to clear these motion risks before clearing the subject to return to the slopes.

In an embodiment, the method of the system is used to collect initial assessment data for subjects complaining of any type of physical motion injury. In an embodiment, the method of the system is used to evaluate a subject performing a therapeutic regimen to assess whether or not the regimen needs tailoring based on previously unknown injuries or motion tendencies of the patient as the regimen is performed. In an embodiment, the method of the system is used to evaluate a subject performing a training regimen designed to improve physical ability, endurance, agility, or strength. In an embodiment, the method of the system is used for the collection of data using a regimen that is similar to a standard regiment but tailored to individual limitations. In an embodiment, a set of K physical exercises is treated by the system as sufficiently similar to be classified as the same regimen for the purposes of data clustering and subject sample evaluation.

The embodiment illustratively depicted in FIG. 2 may be used for generating a bicluster classifier and verifying and validating whether such a detector achieves statistical sensitivity and specificity in the intended range of deployment that is sufficient for satisfactory performance in the use for classifying patients according to injury/recovery outcome. Quantile thresholds are employed to produce a multi-level ordinal score as a function of each monitored continuous or discrete motion variable. In an embodiment, this has the effect of removing data noise and placing the various signals on a unified measurement scale before calculating and updating the bicluster classifications. Instructions carried on a computer-readable storage medium (e.g., for calculating quantile scores) can be implemented in a high level procedural or object oriented programming language to communicate with a computer system. Instructions can be implemented in assembly or machine language. Instructions can be implemented in a compiled or interpreted language.

By way of example, an embodiment of a method of the system was used to study 268 experimental ambulatory subjects between the ages of 22 and 61. Each subject was independently evaluated (a) by one certified trainer/kinesiologist in one testing facility and (b) by a method of a system in the same testing facility from 3-D motion-capture data collected on the same date. One hundred forty-nine (56%) of the subjects had experienced one or more historical musculoskeletal injuries, many of them associated with residual pain. The injuries were often solitary (single body part); however, 78 were amateur athletes who presented with a history of injury to two or more body parts. The injury conditions included Achilles tendinitis, Achilles tendon tear, Ankle fracture, Ankle sprain, Anterior compartment syndrome, Asymmetric leg length, Calcaneus fracture, Chondromalacia of knee, Colles fracture of forearm, Fracture of femur, Fracture of cervical spine, Fracture of pelvis, Glenohumeral joint instability, Gout, Hamstring injury, Herniated intervertebral disc, Hip adductor injury, Hip subluxation, Iliotibial band syndrome of knee, Inguinal hernia, Lumbar spine injury, Meniscus tear of knee, Metatarsal fracture, Osgood-Schlatter of knee, Osteoarthritis of hip, Osteoarthritis of knee, Patella injury, Quadriceps injury, S/P anterior cruciate ligament repair, S/P rotator cuff repair, S/P total hip replacement, S/P total knee replacement, Sciatica, Scoliosis, Shoulder avulsion, and Shoulder subluxation. The remaining 119 (44%) of the subjects (controls) were healthy and injury-free.

A multi-camera, high-speed digital video 3-D motion capture system from Dynamic Athletics Inc. was used to measure 135 biomechanics variables (starting and ending angles; torques about joints; forces; velocities) as subjects executed a standardized series of maneuvers, including squat-jumps, lunges, and other movements such as are customary in evaluations by kinesiologists, sports trainers, physical therapists, and rehabilitation medicine physicians. To eliminate a bias towards markers exhibiting wide dynamic range values distributions, the marker matrix was transformed by separate quantile scalings for each marker to equalize their norms. Although non-negative factorizations have the advantage of obtaining sparse and readily interpretable matrix decompositions, such factorizations may not directly account for skewedness or abnormal diminution of the dynamic range of variables' values. To deal with such attenuation, we extend the biomarker matrix with low-quantile markers.

In an embodiment, factor analysis for bicluster acquisition (FABIA) biclustering is utilized to identify marker-condition and condition-subject clusters. In an embodiment, to avoid over-fitting one may select and optimize the number of biclusters Nc as the number of dimensions around which the change in relative error $d\varepsilon/dNc$ of the factorization of the real data reaches from above the change in relative error obtained for a randomized data set or by other suitable means. In the reduction to practice involving the cohort of 268 subjects, optimal Nc was equal to four biclusters. An embodiment of the computation of biclusters is shown in greater detail in the computer program routine shown in FIGS. 5A-5B.

The system accurately classified musculoskeletal abnormalities, as shown in display 400 of FIG. 4, where the mean weighted Cohen's kappa is x=0.82, indicating excellent agreement of the system with the kinesiologist. Cluster_01 detects clavicular/glenohumeral abnormalities; cluster_02 comprises uni/squat variables and measures deficits in lower-extremity force-development; cluster_03 reveals interactions among trunk-thorax-lumbar spine; and cluster_04 comprises uni/lunge/squat variables and encompasses twelve biomarkers that primarily relate to lower-extremity stability, balance, and range of motion.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

Accordingly, in a one aspect, a method is provided for movement risk evaluation. The method comprises: collecting a set of 3-D motion data of a test subject performing a first regimen of physical motion; measuring a subject array comprising motion variables derived from said set of 3-D motion data; forming an expert database comprising a set of N reference arrays, each said reference array comprising motion variables measured from a set of 3-D motion data of a reference subject performing a regimen of physical motion; identifying one or more clusters within said expert database using a biclustering technique; evaluating said subject array to identify a chosen cluster associated with said subject array; and presenting on a computer display data associated with said chosen cluster to alert a computer user to one or more potential motion risks relevant to said test subject.

In some embodiments, the method further comprises: characterizing one or more of said one or more clusters within said expert database; and/or collecting a set of biological health data associated with said test subject, wherein said subject array comprises measurements derived from said set of biological health data. In some embodiments, the set of biological health data comprises data derived from biological health sensors operative proximate to a time of said collecting of said set of 3-D motion data of a test subject performing said first regimen of physical motion; or the set of biological health data comprises data derived from biological health sensors operative during a time of said collecting of said set of 3-D motion data of a test subject performing said first regimen of physical motion. In some embodiments, the biological health data comprises one or more of blood pressure, blood oxygen measure, heart rate, respiration rate, audio, temperature, gender, age, ability, weight, body mass index, flexibility, body size, athletic level; the data associated with said chosen cluster comprises a proper subset of variables of said subject area identified by said biclustering technique; the proper subset of variables has a dimensionality of less than one quarter of the dimensionality of the subject array; the data associated with said chosen cluster comprises an order set associated with the chosen cluster; forming of the expert database comprises forming from a parent database while eliminating one or more reference arrays based on a dissimilarity of said one or more reference arrays based on one or more of identity, origin, gender, age, level of fitness, body size, flexibility, athletic ability, injury status, time since injury, therapeutic regimen prescribed, regimen purpose, regimen class, regimen type, time since therapeutic regimen has been practiced, and diagnostic category; and/or forming of the expert database comprises forming from a parent database by selecting one or more reference arrays based on a similarity of said one or more reference arrays based on one or more of identity, origin, gender, age, level of fitness, body size, flexibility, athletic ability, injury status, time since injury, therapeutic regimen prescribed, regimen purpose, regimen class, regimen type, time since therapeutic regimen has been practiced, and diagnostic category.

In some embodiments, the method further comprises imputing one or more values of variables that are missing using one or more of a last observation carry forward method, a data simulation method, a bootstrap method, and a generalized estimating equation method. In some embodiments, measuring said subject array comprises processing two or more trial repetition arrays to produce one or more elements of said subject array; processing of said two or more trial repetition arrays comprises at least one of a computation of a trial array mean, a use of a trial count, a use of a rank order, and a composition of trial elements; the first regimen is selected from the set consisting of an athletic performance regimen, a flexibility regimen, an assessment regimen, a standard therapeutic regimen, a tailored therapeutic regimen, and a training regimen; the data associated with said chosen cluster comprises data derived from a set of samples that are determined to be representative of said chosen cluster; the data associated with said chosen cluster comprises at least one of an injury category frequently occurring within said chosen cluster and an injury occurring frequently within said chosen cluster; and/or the regimen of physical motion is a regimen drawn from a set of L physical exercises each of which physical exercises are sufficiently similar to said first regimen.

In another aspect, a method is provided for extracting information from a biomechanics data set and determining marker-condition biclusters. The method comprises: creating a first set of clusters of related biomechanics motion data from a first subspace of data in a data set; creating a second set of clusters of related biomechanics motion data from at least a second subspace of data in the data set; determining local relationships between the first set of clusters and the second clusters; associating the first cluster of samples with a first set of conditions and creating a first cluster of variables associated with the first cluster of samples; and associating a second cluster of samples with a second set of conditions and creating a second cluster of variables associated with the second cluster of samples.

In some embodiments of the method, data are selected from a group of 3-D motion-capture biomechanics data acquired during execution of specific body movements by a human subject; and/or data are biomechanics data derived from a plurality of serialized sessions during which biomechanics data are acquired from the same subject over a period of time. In some embodiments, the method further comprises performing data transformation(s), such as scaling, normalization or quantile transformation in the marker-variables dimension; determining marker-condition clusters for each of a plurality of marker-condition blocks, and testing whether biclusters found in a given block extend into data in another block; outputting located biclusters for the plurality of blocks; and/or detecting and deleting duplicated biclusters; producing marker-condition biclusters that denote diagnostic categorizations of movement abnormalities; determining a bicluster membership score based on a plurality of marker measurements; eliminating anomalous values following movement mis-execution occurrences; determining biclusters by a method involving one or more of CTWC, OPSM, ISA, BIMAX, RAP, COALESCE, QUBIC, SAMBA, FABIA, spectral clustering, SSVD, and S4VD; outputting of located biclusters and bicluster membership by communicating to an electronic health record system for storage and retrieval by users; outputting of located biclusters and bicluster membership by communicating to an online decision-support system for further processing, interpretation of findings, and electronic alerting of users; inputting the first cluster into the first cluster and creating a second cluster, including but not limited to, iteratively; and/or inputting the second cluster into the first cluster and creating a second cluster, including but not limited to, iteratively.

In some embodiments of the method, the data corresponds to a two-dimensional array, and wherein each block of a plurality of separate blocks extends across an entire length of the two-dimensional array in a first direction and a part of the length of the two-dimensional array in a second direction; a first bicluster comprising a first sample cluster and a first variable cluster overlaps in data with a second bicluster comprising a second sample cluster and a second variable cluster; the data are selected from a group of 3-D motion-capture biomechanics data acquired during execution of specific body movements by a human subject; and/or the data are biomechanics data derived from a plurality of serialized sessions during which biomechanics data are acquired from the same subject over a period of time.

What is claimed is:

1. A system comprising:
    a three-dimensional (3-D) motion capture system;
    at least one processor; and
    one or more computer storage media storing computer-readable instructions that, when executed by the processor, cause the processor to perform operations comprising:
        capturing from the 3-D motion capture system a set of movements for reference subjects performing a regimen of physical motion;
        generating an index comprising a first data dimension associated with biomechanics motion data determined from the captured set of movements and a second data dimension associated with motion variables, each reference subject having an associated variable array of at least a portion of the biomechanics motion data for the motion variables; and
        creating biclusters from the biomechanics motion data using a biclustering technique on the generated index, wherein the generated index predicts a musculoskeletal injury of a test subject performing the regimen of physical motion based on association of the test subject with at least one bicluster.

2. The system of claim 1, wherein creating the biclusters comprises simultaneously producing marker-condition clusters and condition-subject clusters.

3. The system of claim 1, further comprising a physiological variable probe configured to measure physiological data of the reference subjects, wherein the second data dimension is further associated with physiological variables, and wherein the associated variable array for each reference subject comprises measured physiological data of a reference subject of the reference subjects.

4. The system of claim 1, further comprising removing a selected variable array from the generated index, wherein the biclusters are created from the generated index without the selected variable array.

5. The system of claim 1, further comprising receiving a test subject variable array comprising at least a portion of the biomechanics motion data that is associated with the test subject, wherein the biclusters are created from the generated index and the test subject variable array.

6. The system of claim 1, further comprising:
    employing a quantile threshold to determine a score for each of the motion variables; and
    prior to creating the biclusters from the generated index, removing a portion of the biomechanics motion data based on the quantile threshold score.

7. The system of claim 1, wherein the biclustering technique comprises one of Coupled Two-Way Clustering (CTWC), Order Preserving Submatrix (OPSM), Iterative Signature Algorithm (ISA), Binary Inclusion Maximal algorithm (BIMAX), association analysis based Range Support Patterns (RAP), Combinatorial Algorithm for Expression and Sequence-Based Cluster Extraction (COALESCE), Qualitative Biclustering (QUBIC), Statistical-Algorithmic Method for Bicluster Analysis (SAMBA), Factor Analysis for Bicluster Acquisition (FABIA), spectral clustering, Sparse Singular Value Decomposition (SSVD), or sparse singular value decomposition incorporating stability selection (S4VD).

8. A computer-implemented method comprising:
    receiving biomechanics motions data associated with a set of movements of reference subjects performing a regimen of physical motion captured by a three-dimensional (3-D) motion capture system;

generating an index comprising a first data dimension associated with the biomechanics motion data and a second data dimension associated with motion variables, each reference subject having an associated variable array comprising at least a portion of the biomechanics motion data;

creating biclusters from the biomechanics motion data using a biclustering technique on the generated index; and providing the generated index to predict a musculoskeletal injury of a test subject performing the regimen of physical motion based on association of the test subject with at least one bicluster.

9. The method of claim 8, wherein creating the biclusters comprises simultaneously producing marker-condition clusters and condition-subject clusters.

10. The method of claim 8, wherein the second data dimension is further associated with physiological variables, and wherein the associated variable array for each reference subject comprises measured physiological data of a reference subject of the reference subjects.

11. The method of claim 8, further comprising removing a selected variable array from the generated index, wherein the biclusters are created from the generated index without the selected variable array.

12. The method of claim 8, further comprising receiving a test subject variable array of at least the portion of the biomechanics motion data associated with the test subject, wherein the biclusters are created from the generated index and the test subject variable array.

13. The method of claim 8, further comprising:
employing a quantile threshold to determine a score for each of the motion variables; and
prior to creating the biclusters from the generated index, removing a portion of the biomechanics motion data based on the quantile threshold score.

14. The method of claim 8, wherein the biclustering technique comprises one of Coupled Two-Way Clustering (CTWC), Order Preserving Submatrix (OPSM), Iterative Signature Algorithm (ISA), Binary Inclusion Maximal algorithm (BIMAX), association analysis based Range Support Patterns (RAP), Combinatorial Algorithm for Expression and Sequence-Based Cluster Extraction (COALESCE), Qualitative Biclustering (QUBIC), Statistical-Algorithmic Method for Bicluster Analysis (SAMBA), Factor Analysis for Bicluster Acquisition (FABIA), spectral clustering, Sparse Singular Value Decomposition (SSVD), or sparse singular value decomposition incorporating stability selection (S4VD).

15. A computer-implemented method comprising:
receiving biomechanics motions data associated with a set of movements of reference subjects performing a regimen of physical motion captured by a three-dimensional (3-D) motion capture system, wherein a portion of the reference subjects have a known musculoskeletal injury;

generating an index comprising a first data dimension associated with the biomechanics motion data and a second data dimension associated with motion variables, each reference subject having an associated variable array comprising at least a portion of the biomechanics motion data for the motion variables;

creating biclusters from the biomechanics motion data using a biclustering technique on the generated index;

associating the known musculoskeletal injury to a bicluster; and providing the generated index to predict a musculoskeletal injury of a test subject performing the regimen of physical motion based on association of the test subject with the bicluster associated with the known musculoskeletal injury.

16. The method of claim 15, wherein creating the biclusters comprises simultaneously producing marker-condition clusters and condition-subject clusters.

17. The method of claim 15, wherein the second data dimension is further associated with physiological variables, and wherein the associated variable array for each reference subject comprises measured physiological data of a reference subject of the reference subjects.

18. The method of claim 15, further comprising removing a selected variable array from the generated index, wherein the biclusters are created from the generated index without the selected variable array.

19. The method of claim 15, further comprising receiving a test subject variable array of at least a portion of the biomechanics motion data associated with the test subject, wherein the biclusters are created from the generated index and the test subject variable array.

20. The method of claim 15, further comprising:
employing a quantile threshold to determine a score for each of the motion variables; and
prior to creating the biclusters from the generated index, removing a portion of the biomechanics motion data based on the quantile threshold score.

* * * * *